United States Patent [19]

Hirai

[11] Patent Number: 6,133,488
[45] Date of Patent: *Oct. 17, 2000

[54] PROCESSES FOR SEPARATING ADAMANTANOLS

[75] Inventor: Naruhisa Hirai, Himeji, Japan

[73] Assignee: Daicel Chemical Industries, Limited, Osaka, Japan

[ * ] Notice: This patent issued on a continued prosecution application filed under 37 CFR 1.53(d), and is subject to the twenty year patent term provisions of 35 U.S.C. 154(a)(2).

[21] Appl. No.: 08/962,308

[22] Filed: Oct. 31, 1997

[30] Foreign Application Priority Data

Nov. 21, 1996 [JP] Japan ..................... 8-310846

[51] Int. Cl.⁷ .................................. C07C 35/22
[52] U.S. Cl. ................ 568/818; 568/817; 568/808; 585/352
[58] Field of Search ................ 568/808, 817, 568/818, 836; 548/473; 585/352

[56] References Cited

U.S. PATENT DOCUMENTS

| | | | |
|---|---|---|---|
| 3,356,740 | 12/1967 | Schneider et al. | 260/617 |
| 3,356,741 | 12/1967 | Schneider et al. | 260/617 |
| 3,594,427 | 7/1971 | Moore | 260/619 R |
| 3,753,950 | 8/1973 | Thompson | 260/49 |
| 3,832,332 | 8/1974 | Thompson | 260/78 R |
| 4,990,691 | 2/1991 | Honna et al. | 568/818 |
| 5,268,513 | 12/1993 | Shen et al. | 568/818 |

FOREIGN PATENT DOCUMENTS

| | | |
|---|---|---|
| 4216621 | 8/1942 | Japan . |
| 4226792 | 12/1942 | Japan . |
| 44-12891 | 10/1969 | Japan . |
| 46-28419 | 8/1971 | Japan . |
| 50-21090 | 3/1975 | Japan . |
| 2196744 | 8/1990 | Japan . |
| 8038909 | 2/1996 | Japan . |

OTHER PUBLICATIONS

Perrin et al, Purification of Laboratory Chemicals, 2nd edition, p. 553, 1980.

*Primary Examiner*—Sreeni Padmanabhan
*Attorney, Agent, or Firm*—Birch, Stewart, Kolasch & Birch, LLP

[57] ABSTRACT

With the use of an aqueous solvent containing at least water (e.g. water), and at least one organic solvent selected from esters or ketones and separable from the aqueous solvent, the processes of the invention separate (1) an adamantanediol and an adamantanepolyol having three or more hydroxyl groups per molecule, from a group of adamantanepolyols having plural hydroxyl groups per molecule, distributing the former into an organic solvent layer and the latter into an aqueous solvent layer. Further, (2) an adamantanemonool and the group of adamantanepolyols can be separated from a group of adamantanols having at least one hydroxyl group per molecule with using an aqueous solvent (e.g. aqueous solution of acetic acid) for crystallization of the adamantanemonool.

13 Claims, No Drawings

PROCESSES FOR SEPARATING ADAMANTANOLS

FIELD OF THE INVENTION

The present invention relates to processes for separating a group of adamantanols which are useful as highly functionalized materials such as an optical fiber or raw materials for medicines and agricultural chemicals.

BACKGROUND OF THE INVENTION

It is known that adamantane shows distinctive functions because of its three-dimensionally symmetric structure, where each ring is mutually stabilized. A variety of highly functionalized copolymers (copolymers having enhanced or improved functions or characteristics) can be obtained by introducing a hydroxyl group into adamantane, and, if necessary, deriving it into an acrylic acid derivative or a carbonate. There have been suggested many processes for producing copolymers from a hydroxyl group-introduced adamantane, such copolymers including polyesters (Japanese Patent Application Laid-open No. 21090/1975 (JP-A-50-21090), etc.), polycarbonates (U.S. Pat. No. 3,594, 427, etc.), polyamides and polyimides (U.S. Pat. No. 3,832, 332, etc.), polyurethanes (Japanese Patent Publication No. 12891/1969 (JP-B-44-12891), etc.), polysulfones and polysulfonates (U.S. Pat. No. 3,753,950, etc.), vinyl polymers (Japanese Patent Publication No. 28419/1971 (JP-B-46-28419), etc.), and the like.

The polymers obtainable from adamantane derivatives, which generally have excellent functions or characteristics (high functionality), are by far superior to conventional polymers in optical characteristics such as small light-inducing loss, high refractive index and double refraction index, and other characteristics including moisture-resistance, heat-resistance, coefficient of thermal expansion, etc. Accordingly, there have been some attempts to make use of these polymers as optical fibers, optical elements, optical lenses, holograms, optical discs, contact lenses and other optical materials, transparent resin coating compositions for organic glasses, electric conductive polymers, photosensitive materials, fluorescent materials and so forth.

Incidentally, an amino derivative derived from an alcohol derivative of adamantane is useful for introducing various medicines having excellent pharmacological activity or agricultural chemicals, such as "SYMMETREL" (trade name), a therapeutic agent for Parkinson's disease.

As described above, hydroxyl group-containing adamantanes, particularly adamantanepolyols having hydroxyl groups at plural bridgehead positions, are utilized in a broad range of applications.

Japanese Patent Publication No. 16621/1967 (JP-B-42-16621) suggests the use of chromic acid for the production of a group of adamantanepolyols. According to this process, an adamantanediol can be obtained, almost quantatively, from adamantane in a single step. However, this process requires an excess amount of expensive chromic acid and complicated post-treatments. Besides, even under severe reaction conditions, it is difficult to produce an adamantanetriol or a higher adamantanepolyol.

Japanese Patent Publication 26792/1967 (JP-B-42-26792) discloses a process which comprises oxidizing a molten adamantane with oxygen using a cobalt salt catalyst for the production of an adamantanediol. However, its selectivity is critically low, and a higher conversion causes the formation of by-products such as ketone derivatives. Additionally, this literature teaches a process for separating and purifying an adamantanediol from the reaction mixture, based on the fact that the adamantanediol has a different degree of solubility in a hydrocarbon or ether from that of the other components (e.g. by-products, raw materials).

In Japanese Patent Application Laid-open No. 196744/1990 (JP-A-2-196744), a tribromoadamantane is hydrolysed to give an adamantanepolyol. In this process, however, it is difficult to produce a tribromoadamantane. Besides, since the tribromoadamantane is lost in the hydrolysis step in a large quantity, the yield of an adamantanetriol is miserably low.

Japanese Patent Application Laid-open No. 38909/1996 (JP-A-8-38909) discloses a process comprising oxidation of a substrate with oxygen using an imide compound catalyst. By oxidizing a substrate such as adamantane, according to this process, monools, diols, triols, tetraols and other polyols of adamantane can be produced at a high conversion and selectivity even under mild or moderate conditions. However, it is extremely difficult to separate, in an efficient manner, these adamantanemonool, adamantanediol, and adamantanepolyols among themselves, as each of them has closely similar chemical properties to those of the others.

SUMMARY OF THE INVENTION

It is, therefore, an object of the present invention to provide a process for efficiently separating an adamantanediol, and an adamantanepolyol having at least three hydroxyl groups per molecule, from a group of adamantanepolyols each having a plurality of hydroxyl groups per molecule.

An other object of the present invention is to provide a process for separating an adamantanediol and an adamantanepolyol having at least three hydroxyl groups per molecule from each other, by a simple operation under moderate conditions.

A further object of the present invention is to provide a process for efficiently separating an adamantanediol, and an adamantanepolyol having at least three hydroxyl groups per molecule, from a reaction mixture which is obtained by an oxidation reaction conducted in the presence of an imide compound for the production of a group of adamantanepolyols each having a plurality of hydroxyl groups per molecule at a high conversion and selectivity.

It is a still another object of the present invention to provide an efficient process for separating an adamantanemonool, and a group of adamantanepolyols each having a plurality of hydroxyl groups per molecule, from a group of adamantanols each having at least one hydroxyl group per molecule.

It is a still further object of the present invention to provide a process for separating an adamantanemonool and a group of adamantanepolyols each having a plurality of hydroxyl groups per molecule from each other, by a simple operation under moderate conditions.

It is a yet another object of the present invention to provide an efficient process for separating an adamantanemonool, an adamantanediol, and an adamantanepolyol having at least three hydroxyl groups per molecule, from an oxidation reaction mixture containing these three components.

The inventor of the present invention worked intensively to achieve the above objects, and found that:

(1) an adamantanediol and an adamantanepolyol having at least three hydroxyl groups can be efficiently separated from each other by extraction of a group of adamantanepolyols having a plurality of hydroxyl groups per molecule with a combined use of some specific solvents; and (2) any of (i) an adamantanemonool, (ii) an adamantanediol, or (iii) a group of adamantanepolyols each having a plurality of hydroxyl groups per molecule can be crystallized with a selective use of some specific solvents, thereby being separated from the others in an efficient manner.

The present invention is based on the above findings.

One of the separation processes of the present invention is a process for separating an adamantanediol, and an adamantanepolyol having at least three hydroxyl groups per molecule, from a group of adamantanepolyols each having a plurality of hydroxyl groups per molecule. With the use of an aqueous solvent containing at least water (hereinafter it may be referred to as "aqueous solvent") and at least one organic solvent selected from esters or ketones (hereinafter, it may be referred to as "separation solvent"), the adamantanepolyol and the adamantanediol are separately distributed into a layer of the aqueous solvent and a layer of the separation solvent, respectively.

Another separation process of the present invention is a process for separating an adamantanediol, and an adamantanepolyol having at least three hydroxyl groups per molecule, from a heated aqueous solution containing a group of adamantanepolyols each having a plurality of hydroxyl groups per molecule, by crystallization of the adamantanediol using the aqueous solvent.

A group of adamantanepolyols each having plural hydroxyl groups per molecule can be obtained, as non-eluted components, by washing or extraction of a reaction mixture with using at least one organic solvent selected from ethers or hydrocarbons (hereinafter, it may be mentioned as "washing solvent"), the reaction mixture being obtained by oxidation of an optionally substituted adamantane such as adamantane or an adamantanemonool (hereinafter, it may be mentioned as "a group of adamantanes") with oxygen in the presence of an imide compound such as N-hydroxyphthalimide.

A further separation process of the present invention is a process for separating an adamantanemonool, and a group of adamantanepolyols each having a plurality of hydroxyl groups per molecule, from a group of adamantanols having at least one hydroxyl group per molecule. According to this process, the adamantanemonool is crystallized out of an aqueous solution containing the group of adamantanols each having at least one hydroxyl group per molecule, with the use of the aqueous solvent at least containing water.

A still another separation process of the present invention is a process for separating an adamantanemonool, and a group of adamantanepolyols each having a plurality of hydroxyl groups per molecule, from a group of adamantanols each having at least one hydroxyl group per molecule. With the use of at least one organic solvent selected from esters, ketones or cyclic ethers, the group of adamantanepolyols each having plural hydroxyl groups per molecule is crystallized out of the organic solvent solution which contains the group of adamantanols each having at least one hydroxyl group per molecule.

A still further separation process of the invention is a process for separating an adamantanemonool, and a group of adamantanepolyols each having a plurality of hydroxyl groups per molecule, from a group of adamantanols each having at least one hydroxyl group per molecule. This process comprises employing an organic solvent having a solubility parameter δ of 7.7 to 12.2 ($cal^{1/2}/cc^{1/2}$), whereby the group of adamantanepolyols each having a plurality of hydroxyl groups per molecule is crystallized out of a solution of the organic solvent containing the group of adamantanols each having at least one hydroxyl group per molecule.

The present invention further includes a process for separating an adamantanemonool, an adamantanediol, and an adamantanepolyol having at least three hydroxyl groups per molecule, from a group of adamantanols having at least one hydroxyl group per molecule. This process comprises:

a crystallization step of treating an oxidation reaction mixture using the aqueous solvent containing at least water, for crystallization of an adamantanemonool, and an extraction step, after the recovery of the adamantanemonool, of adding, to the remaining mixture, an organic solvent which is selected from esters or ketones and separable from water, for separate distribution of the adamantanediol into a layer of the organic solvent and the adamantanepolyol into a layer of the aqueous solvent, the reaction mixture being obtained by oxidizing at least one substrate selected from the group consisting of adamantane and adamantanemonools in the presence of an imide compound shown by the following formula (1),

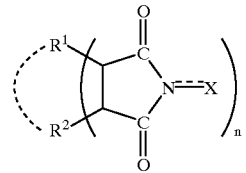

(1)

wherein $R^1$ and $R^2$ represent, same or different, a hydrogen atom, a halogen atom, an alkyl group, an aryl group, a cycloalkyl group, a hydroxyl group, an alkoxy group, a carboxyl group, an alkoxycarbonyl group or an acyl group; $R^1$ and $R^2$ may bond together to form a double bond or an aromatic or non-aromatic ring; X stands for an oxygen atom or a hydroxyl group; and n is an integer of 1 to 3.

Throughout the present specification, it should be understood that "adamantane derivatives each having at least one hydroxyl group per molecule" may be simply referred to as "a group of adamantanols," while "a group of adamantanepolyols each having a plurality of hydroxyl groups per molecule" may be mentioned as "a group of adamantanepolyols." In addition, "an adamantanepolyol having at least three hydroxyl groups per molecule" may be called "an adamantanepolyol," and "an adamantanemonool" may be referred to as "an adamantanol."

DETAILED DESCRIPTION OF THE INVENTION

[A Group of Adamantanepolyols]

A group of adamantanepolyols includes an adamantanediol, an adamantanetriol, an adamantanetetraol and the like. This group of adamantanepolyols may have hydroxyl groups at any positions, and there may be mentioned, for example, 1,3-adamantanediol, 1,3,5-adamantanetriol and 1,3,5,7-adamantanetetraol.

Adamantanediols and adamantanetriols may optionally have substituents at any positions. Taking adamantanetriols as an example, a substituted adamantanetriol can be represented by the following formula (2),

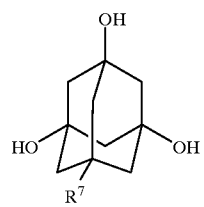

(2)

wherein $R^7$ represents an alkyl group, an aryl group, a cycloalkyl group, an alkoxy group, an aryloxy group, or an acyloxy group.

The alkyl group includes, for instance, methyl, ethyl, propyl, butyl, hexyl, octyl, decyl and other $C_{1-10}$ alkyl groups, preferably $C_{1-6}$ alkyl groups, and particularly $C_{1-4}$ alkyl groups. The aryl group includes a phenyl group, a naphthyl group, and the like. The cycloalkyl group includes a cyclohexyl group, a cyclooctyl group, and so on.

The alkoxy group includes, for instance, methoxy, ethoxy, propoxy, butoxy, pentyloxy, hexyloxy and other $C_{1-10}$ alkoxy groups. The aryloxy group includes a phenoxy group and the like. The acyloxy group includes acetyloxy, propionyloxy, butyryloxy and other $C_{2-6}$ acyloxy groups.

The group of adamantanepolyols is obtainable by hydrolysis of adamantane having plural bromine atoms, such as dibromo- and tribromo-adamantanes. A preferable production process includes a process which comprises oxidation of an optionally substituted adamantane (a group of adamantanes: adamantane, adamantanemonool, etc.) with oxygen in the presence of an imide compound (e.g. N-hydroxyphthalimide) of the above formula (1) as a catalyst, for the production of a group of adamantanepolyols (Japanese Patent Application Laid-open No. 38909/1996 (JP-A-8-38909)). The imide compound to be used herein includes the compounds shown by the above formula (1).

In the formula (1), the halogen atom, as the substituents $R^1$ and $R^2$, includes iodine, bromine, chlorine and fluorine atoms. The alkyl group includes, for example, methyl, ethyl, propyl, isopropyl, butyl, isobutyl, sec-butyl, t-butyl, pentyl, hexyl and other $C_{1-10}$ alkyl groups, preferably $C_{1-6}$ alkyl groups, and particularly $C_{1-4}$ alkyl groups. As the aryl groups, there may be mentioned, for instance, a phenyl group and a naphthyl group. Examples of the cycloalkyl group include cyclopentyl, cyclohexyl, and cyclooctyl groups.

The alkoxy group includes, for example, methoxy, ethoxy, propoxy, isopropoxy, butoxy, isobutoxy, t-butoxy, pentyloxy, hexyloxy, and other $C_{1-10}$ alkoxy groups, preferably $C_{1-6}$ alkoxy groups, and particularly $C_{1-4}$ alkoxy groups. Examples of the alkoxycarbonyl group include methoxycarbonyl, ethoxycarbonyl, propoxycarbonyl, isopropoxycarbonyl, butoxycarbonyl, isobutoxycarbonyl, t-butoxycarbonyl, pentyloxycarbonyl, hexyloxycarbonyl, and other $C_{1-10}$ alkoxy-carbonyl groups, preferably $C_{1-6}$ alkoxy-carbonyl groups, and particularly $C_{1-4}$ alkoxy-carbonyl groups. The acyl group includes, for instance, formyl, acetyl, propionyl, butyryl, isobutyryl, valeryl, isovaleryl, pivaloyl, and other $C_{1-6}$ acyl groups.

The substituents $R^1$ and $R^2$ may be either the same or different from each other. In the formula (1), $R^1$ and $R^2$ may bond together to form a double bond, or an aromatic or non-aromatic ring. A preferred aromatic or non-aromatic ring may be a ring of about 5 to 12 members, in particular about 6 to 10 members. The ring may practically be a hydrocarbon ring, although it may be a heterocyclic ring or a condensed heterocyclic ring. As such a ring, there may be mentioned, for instance, non-aromatic alicyclic rings (e.g. optionally substituted cycloalkane rings such as a cyclohexane ring, optionally substituted cycloalkene rings such as a cyclohexene ring), non-aromatic bridged rings (e.g. 5-norbornene ring and other optionally substituted bridged hydrocarbon rings), and optionally substituted aromatic rings such as a benzene ring and a naphthalene ring. The ring may practically comprise an aromatic ring.

Preferred imide compounds include the ones shown by the following formula (1a) to (1f),

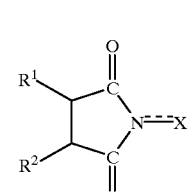

(1a)

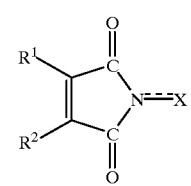

(1b)

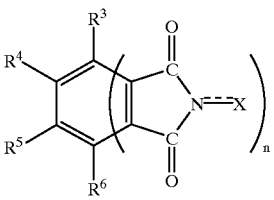

(1c)

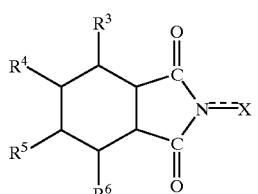

(1d)

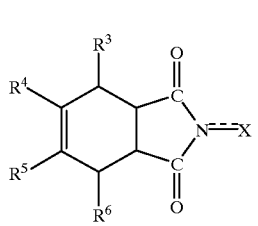

(1e)

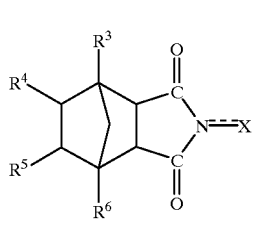

(1f)

wherein $R^3$, $R^4$, $R^5$ and $R^6$ independently represent a hydrogen atom, an alkyl group, a hydroxyl group, an alkoxy group, a carboxyl group, an alkoxycarbonyl group, an acyl group, a nitro group, a cyano group, an amino group or a halogen atom; and $R^1$, $R^2$ and n have the same meanings as defined above.

In the substituents $R^3$, $R^4$, $R^5$ and $R^6$, the alkyl group, the alkoxy group, the alkoxycarbonyl group, the acyl group, and the halogen atom are similar to the substituents and atoms as exemplified above.

The substituents $R^3$, $R^4$, $R^5$ and $R^6$ may practically be hydrogen atoms, alkyl groups having about 1 to 4 carbon atoms, carboxyl groups, nitro groups or halogen atoms.

The symbol X in the formula (1) denotes an oxygen atom or a hydroxyl group. The symbol n usually denotes about 1 to 3, preferably 1 or 2. The imide compound shown by the formula (1) can be used singly or in combination in the oxidation reaction.

Examples of desirable imide compounds include imide compounds derived from an aliphatic polycarboxylic acid anhydride (e.g. N-hydroxysuccinimide, N-hydroxymaleimide), imide compounds derived from an alicyclic polycarboxylic acid anhydride or an aromatic polycarboxylic acid anhydride (e.g. N-hydroxyhexahydrophthalimide, N,N'-dihydroxycyclohexanetetracarboximide, N-hydroxyphthalimide, N-hydroxytetrabromophthalimide, N-hydroxytetrachlorophthalimide, N-hydroxyhetimide, N-hydroxyhimimide, N-hydroxytrimellitimide, N,N'-dihydroxypyromellitimide, N,N'-dihydroxynaphthalenetetracarboximide), and so forth. These imide compounds have high oxidizing properties. Among these, an N-hydroxyimide compound derived from an alicyclic polycarboxylic acid anhydride, particularly from an aromatic polycarboxylic acid anhydride, such as N-hydroxyphthalimide, is particularly preferred.

The imide compound can be prepared by a conventional imitation process (a process for the formation of an imide), such as a process which comprises the steps of reacting a corresponding acid anhydride with hydroxylamine $NH_2OH$ for ring-opening of an acid anhydride group, and closing the ring for imide formation.

The oxidation catalyst may comprise either the imide compound of the formula (1) alone, or the imide compound of the formula (1) and a co-catalyst. The co-catalyst includes a catalyst comprising a transition metal compound (e.g. oxide, organic acid salt, inorganic acid salt, halide, complex, heteropoly acid or its salt) or a boron compound.

Co-oxidants (co-oxidizing agents) to be used as the co-catalyst include a metal compound, such as a transition metal compound, and a compound containing a Group 13 element of the Periodic Table of Elements (e.g. boron B, aluminium Al) including a boron compound. These co-oxidants can be used alone or in combination.

The co-catalyst may practically be a metal oxide containing a transition metal element inclusive of Groups 3 to 11 elements of the Periodic Table of Elements, in particular Ce, V, Nb, Cr, Mo, W, Mn, Fe, Ru, Co, Rh, Ni, and Cu; a double oxide or an oxygen acid salt; an organic acid salt; an inorganic acid salt; a halide; a coordinate compound (complex) containing the above metal elements; or a heteropoly acid or a salt thereof.

The amount of the imide compound of the formula (1) is selectable from a wide range. For example, its amount is about 0.001 to 1 mole, preferably about 0.001 to 0.5 mole, and more preferably about 0.01 to 0.3 mole, relative to 1 mole of the substrate. The amount may practically be about 0.01 to 0.25 mole relative to 1 mole of the substrate.

The amount of the co-catalyst is selected from a range not to lower the reactivity and selectivity. For example, the amount is about 0.0001 to 0.7 mole, preferably about 0.0001 to 0.5 mole, and more preferably about 0.0001 to 0.3 mole, relative to 1 mole of the substrate. Practically, the co-catalyst is used in about 0.0005 to 0.1 mole.

Oxidation of a group of adamantanes with oxygen using the above oxidation catalyst provides an adamantanol (adamantanemonool), an adamantanediol, an adamantanetriol, an adamantanetetraol and the like. As the oxidation reaction proceeds, an adamantanepolyol is produced in an increasing quantity. For this reason, the production amount of the adamantanol, the adamantanediol, the adamantanetriol, the adamantanetetraol, etc. can be controlled in accordance with the progress of the reaction. Therefore, the above oxidation reaction can efficiently produce an adamantanol, an adamantanediol, and an adamantanepolyol at a high conversion and selectivity.

The oxygen for the oxidation reaction which employs the imide compound of the formula (1) may be active oxygen, but use of molecular oxygen is more advantageous. Such molecular oxygen is not specifically limited, and use may be made of whichever of pure oxygen, or oxygen diluted with an inert gas such as nitrogen, helium, argon or carbon dioxide gas. Air is preferably employed in terms of operability, safety, and economical factors.

The amount of the oxygen can be selected according to the species of the substrate, and is usually about 0.5 mole or more (e.g. 1 mole or more), preferably about 1 to 100 moles, and more preferably about 2 to 50 moles relative to 1 mole of the substrate.

The above-mentioned oxidation process is generally conducted in an inert solvent. As the solvents, there may be mentioned, for example, protonic acids [e.g. organic acids (including carboxylic acids such as formic acid, acetic acid, and propionic acid; hydroxycarboxylic acids such as oxalic acid, citric acid, and tartaric acid; alkyl-sulfonic acids such as methanesulfonic acid and ethanesulfonic acid; arylsulfonic acids such as benzenesulfonic acid and p-toluenesulfonic acid, etc.), inorganic acids (including hydrochloric acid, sulfuric acid, nitric acid, phosphoric acid, etc.)], nitrites (e.g. acetonitrile, propionitrile, benzonitrile), amides (e.g. formamide, dimethylformamide), alcohols (e.g. t-butanol), aliphatic hydrocarbons (e.g. hexane, octane), aromatic hydrocarbons (e.g. benzene, toluene), halogenated hydrocarbons (e.g. chloroform), nitro compounds (e.g. nitromethane, nitrobenzene), esters (e.g. ethyl acetate), ethers (e.g. dimethyl ether, dioxane, tetrahydrofuran), and mixtures of these solvents. Amongst these solvents, protonic acids and nitriles are practically used as such.

The oxidation reaction proceeds smoothly even under comparatively mild or moderate conditions. The reaction temperature, which can be suitably decided according to the species of the imide compound and the substrate, is about 0 to 300° C., preferably about 30 to 250° C., more preferably about 40 to 150° C., and practically about 60 to 120° C. (e.g. 70 to 110° C.). The reaction is carried out at ambient pressure (atmospheric pressure) or under a pressure (under a load). When the reaction is conducted under a pressure, the pressure is usually about 1 to 100 atm (e.g. about 1.5 to 80 atm), preferably about 2 to 70 atm, and more preferably about 5 to 50 atm. The reaction time can be liberally chosen within a range of about 30 minutes to 48 hours, preferably about 1 to 36 hours, and more preferably about 2 to 24 hours, according to the reaction temperature and pressure. The reaction may be effected in the presence of or under a flow of molecular oxygen, in a conventional manner such as a batch system, semi-batch system or continuous system.

[Separation of a Group of Adamantanepolyols and Other Components from the Reaction Mixture]

The reaction mixture obtained in the above reaction contains an unreacted adamantane or its derivatives (e.g. by-products such as adamantanol and adamantanone) in addition to a group of adamantanepolyols. The reaction mixture may further contain the reaction solvent, the catalyst and the co-catalyst. Among them, the reaction solvent is easily removable by distillation or the like.

Prior to the separation of an adamantanediol and an adamantanepolyol, it is advisable to pre-treat the reaction mixture so that the mixture may contain no other components than the group of adamantanepolyols. Incidentally, the components other than the group of adamantanepolyols (hereinafter, they may be referred to as "hydrophobic components") are soluble in at least one organic solvent (washing solvent) selected from ethers or hydrocarbons, whereas the group of adamantanepolyols (hereinafter, they may be referred to as "hydrophilic components") are insoluble in the washing solvent. Therefore, the hydrophobic components can be removed off from the reaction mixture, after the reaction solvent is distilled off, by allowing the remaining reaction mixture to be subjected to washing or extraction with the use of the washing solvent.

The ethers include chain ethers (e.g. dialkyl ethers including dimethyl ether, methyl ethyl ether, methyl isopropyl ether, diethyl ether, ethyl propyl ether, dipropyl ether, diisopropyl ether, dibutyl ether, diisoamyl ether, 1,2-dimethoxyethane, diethylene glycol dimethyl ether), and so on.

The hydrocarbons include aliphatic hydrocarbons (e.g. pentane, hexane, heptane and other saturated hydrocarbons having about 5 to 10 carbon atoms), and others.

The solubility parameter $\delta$ of the washing solvent is about 6.5 to 7.5 ($cal^{1/2}/cc^{1/2}$).

In this pre-treatment (separation process), the hydrophilic components are obtained as a crystal of a mixture of an adamantanediol, an adamantanepolyol, and so on.

The amount of the washing solvent is selected depending on the species of the hydrophobic components (e.g. adamantanol). The proportion of the washing solvent relative to the reaction mixture (the former/the latter, by weight) equals 0.1/1 to 500/1, preferably about 1/1 to 200/1, and more preferably about 2/1 to 100/1.

The frequency of the extraction with the use of the washing solvent is optionally selected, according to the species of the hydrophobic components (e.g. adamantanol), from a range of about 1 to 5 times, preferably about 1 to 3 times (e.g. once or twice). The washing or extraction may be conducted under heating, the temperature therefor being optional in the range of about 0 to 100° C., preferably about 5 to 50° C., and more preferably about 10 to 35° C. For enhanced washing or extraction efficiency, the washing or extraction may be carried out under stirring force or shearing force.

Incidentally, the hydrophobic components may be recovered after being separated by washing or extraction. Each of the hydrophobic components (particularly, unreacted adamantane, adamantanol, adamantanone, and catalyst) can be recovered by a conventional separation method such as filtration, concentration, distillation, crystallization, extraction, recrystallization, column chromatography, and a combination of these. The components thus recovered may be used repeatedly.

[Separation of an Adamantanediol and an Adamantanepolyol (Separation process A)]

The non-eluted components (hydrophilic components) obtained in the pre-treatment include an adamantanediol and an adamantanepolyol (e.g. adamantanetriol and/or adamantanetetraol). The adamantanediol is soluble in not only protonic solvents (e.g. water; carboxylic acids such as acetic acid and propionic acid; alcohols such as methanol, ethanol and propanol) but also organic solvents such as esters and ketones. On the other hand, the adamantanepolyol is soluble in the protonic solvents, but less soluble in the above-mentioned organic solvents. Therefore, when the hydrophilic components are treated by shaking or the like with the combined use of an aqueous solvent containing at least water, plus at least one organic solvent (separation solvent) which is selected from esters or ketones and separable from the aqueous solvent, and then allowed to stand for separation, the adamantanepolyol and the adamantanediol can be separated in two layers, being distributed into the aqueous solvent layer and the separation solvent layer, respectively.

The distribution or extraction methods for the group of adamantanepolyols include:

a process which comprises adding a mixture of the aqueous solvent and the separation solvent to the non-eluted components (hydrophilic components) obtained in the pre-treatment, treating the mixture by shaking or the like, and thereafter standing the mixture for distribution of the adamantanepolyol into the aqueous solvent layer and the adamantanediol into the separation solvent layer; and a process which comprises previously adding a portion or all of either the aqueous solvent or the separation solvent to the hydrophilic component for elution or extraction, and adding the rest of the solvent(s) to the hydrophilic components for layer separation and extraction.

A preferable distribution or extraction process includes a process which comprises adding the separation solvent to an aqueous solvent layer containing dissolved hydrophilic components, treating the mixture by shaking or the like and leaving the mixture standing for layer separation, thereby distributing the adamantanediol into the separation solvent layer.

The above aqueous solvent includes an aqueous solvent which comprises water as a main component, specific examples of which are water, and a mixture of water and other water-soluble organic solvents (e.g. $C_{1-3}$ alcohols such as methanol, ethanol, propanol and isopropanol). The proportion of the water-soluble organic solvent in the solvent mixture can be selected from a range of 1 to 25% by weight, preferably about 1 to 10% by weight, based on the total amount of the solvent mixture. Water is preferred as the aqueous solvent.

The esters include the solvents separable from the aqueous solvent, such as aliphatic carboxylic acid esters (e.g. $C_{2-10}$ aliphatic carboxylic acid-$C_{1-10}$ alkyl esters, particularly $C_{2-3}$ aliphatic carboxylic acid-$C_{1-4}$ alkyl esters, inclusive of methyl acetate, ethyl acetate, propyl acetate, isopropyl acetate, butyl acetate, isobutyl acetate, s-butyl acetate, t-butyl acetate, hexyl acetate, 2-ethylhexyl acetate, methyl propionate, ethyl propionate, butyl propionate, isobutyl propionate, amyl propionate, hexyl propionate, ethyl valerate, ethyl hexanoate and ethyl decanoate; aliphatic carboxylic acid aryl esters inclusive of phenyl acetate and phenyl propionate), aromatic carboxylic acid esters (e.g. $C_{7-8}$ aryl mono- or di-carboxylic acid-$C_{1-6}$ alkyl esters inclusive of methyl benzoate, ethyl benzoate, butyl benzoate, dimethyl phthalate, diethyl phthalate and dibutyl phthalate), etc.

The ketones include the solvents separable from the aqueous solvent, such as aliphatic ketones (e.g. $C_{1-4}$ alkyl- $C_{2-4}$ alkyl ketones inclusive of methyl ethyl ketone, diethyl ketone, methyl propyl ketone, methyl isopropyl ketone, methyl butyl ketone, methyl isobutyl ketone, ethyl propyl ketone, ethyl isopropyl ketone, dipropyl ketone, diisopropyl ketone, and diisobutyl ketone), alicyclic ketones (e.g. $C_{5-10}$ cycloalkanone inclusive of cyclopentanone, cyclohexanone, methyl cyclohexanone, cycloheptanone, and cyclooctanone), and so on.

The solubility parameter δ of the separation solvent is in the range of about 7.7 to 9.7 ($cal^{1/2}/cc^{1/2}$).

The amount of the aqueous solvent can be chosen, depending on the species of the hydrophilic components. For example, the proportion of the aqueous solvent relative to the hydrophilic components (the former/the latter, by weight) is selected from a range of about 0.1/1 to 100/1, preferably about 5/1 to 50/1, and more preferably about 10/1 to 30/1.

The ratio between the aqueous solvent and the separation solvent may be selected in accordance with the species of the hydrophilic components. For instance, the proportion [(aqueous solvent)/(separation solvent), by weight] can be selected from about 10/1 to 0.1/1, preferably about 5/1 to 0.2/1, and more preferably about 3/1 to 0.3/1. In some cases, the separation may be conducted more effectively by employing the separation solvent in a greater ratio than the aqueous solvent [e.g. (aqueous solvent)/(separation solvent) equals about 1/1 to 0.1/1 (by weight)], because the adamantanediol is also soluble in the aqueous solvent.

When an adamantanediol and an adamantanepolyol are contained in at least one layer selected from the aqueous solvent layer or the separation solvent layer, the adamantanediol or the adamantanepolyol can be extracted by a separation operation using the solvent of the other layer (i.e., the aqueous solvent or the separation solvent). The frequency of this extraction is not strictly limited, and is optionally selected from about 1 to 10 times (e.g. 1 to 8 times), preferably about 2 to 8 times (e.g. 2 to 6 times), and more preferably about 3 to 5 times.

The extraction may be carried out under heating. The extraction temperature can be chosen from 0 to 100° C., preferably 5 to 50° C., and more preferably 10 to 35° C., to give an example. For a more effective extraction, the extraction may be carried out under the influence of stirring force or shearing force.

After the extraction, the adamantanepolyol in the aqueous solvent and the adamantanediol in the separation solvent are recovered by a conventional separation method, such as filtration, concentration, distillation, crystallization, extraction, recrystallization, column chromatography, and a combination of these processes.

Additionally, the adamantanediol and the adamantanepolyol may be separated by extraction of the hydrophilic components with the use of the separation solvent, whereby the adamantanediol is extracted into the separation solvent layer.

[Separation of a Group of Adamantanepolyols by Crystallization (Separation Process B)]

The adamantanediol and the adamantanepolyol dissolve in the above aqueous solvent, each of which shows a varying degree of water-solubility according to the changes in temperature. Therefore, the adamantanediol and the adamantanepolyol can be separated from each other by dissolving the hydrophilic components in the aqueous solvent under heating (e.g. at about 40 to 100° C., preferably at about 50 to 80° C.), and then cooling the aqueous solution for crystallization of the adamantanediol.

In this separation process by crystallization, the dissolving temperature can be selected from a wide range of, for example, from 40 to 100° C., and preferably from 50 to 80° C. Generally, the adamantanediol begins to form a crystal (be crystallized) below 20° C. (e.g. about 0 to 15° C., preferably about 0 to 10° C.).

[Separation of an Adamantanol and a Group of Adamantanepolyols by Crystallization (1) (Separation Process C)]

The reaction mixture obtained by the aforesaid oxidation reaction may frequently contain an adamantanol (an adamantanemonool) as an object product or an unreacted component, in addition to the group of adamantanepolyols. A process is hereinafter described for separating the adamantanol and the group of adamantanepolyols from each other.

Each of the adamantanol and the group of adamantanepolyols have such a different degree of solubility in the aqueous solvent. Making use of this difference, the adamantanol and the group of adamantanepolyols can be separated from each other, for instance, by concentrating or cooling a solution (heated, if necessary) containing a mixture of these compounds in the aqueous solvent to give a crystallized adamantanol.

The aqueous solvent for this separation process may be either water, or a mixture of water and a water-soluble organic solvent. As the water-soluble organic solvents, which only need to be soluble in water, there may be mentioned organic carboxylic acids such as formic acid, acetic acid, propionic acid, butyric acid, isobutyric acid, pentanoic acid, hexanoic acid, heptanoic acid, decanoic acid, and dodecanoic acid; ketones such as acetone and cyclohexanone; aliphatic nitriles such as acetonitrile and propionitrile; aliphatic or alicyclic monohydric alcohols such as methanol, ethanol, isopropanol, and cyclohexanol; polyhydric alcohols such as ethylene glycol, propylene glycol, and glycerin; glycol ethers such as ethylene glycol dimethyl ether; cyclic ethers such as tetrahydrofuran and dioxane; non-protonic polar solvents such as N,N-dimethylformamide, dimethylsulfoxide, and pyridine; and others. These organic solvents can be used singly or in combination. Desirable water-soluble organic solvents include organic carboxylic acids having about 1 to 10 (particularly, 2 to 5) carbon atoms, acetone, acetonitrile, $C_{1-3}$ aliphatic monohydric alcohols, and cyclic ethers. A particularly preferred water-soluble organic solvent is a water-soluble solvent which is used as a reaction solvent for the formation of a group of adamantanols (e.g. the above-mentioned oxidation reaction) such as acetic acid or other organic carboxylic acids. Use of this kind of solvent results in the crystallization of an adamantanol by simple processes of concentrating the reaction mixture obtained in the reaction to an appropriate concentration, and adding water to the concentrate.

A preferable aqueous solvent includes a solvent which comprises the water-soluble organic solvent and water in a ratio (the former/the latter, by weight) of about 0/100 to 50/50, preferably about 0/100 to 40/60, and particularly about 5/95 to 30/70.

In this separation process, the temperature for dissolving the adamantanol and the group of adamantanepolyols in the aqueous solvent is, for instance, about 10 to 100° C., and preferably about 15 to 60° C. Where the dissolving temperature is too high, the group of adamantanepolyols is likely to be deteriorated, whereas where the temperature is too low, crystallization efficiency is lowered with the decline of their solubilities. Incidentally, if the aqueous solvent is the mixed solvent of water and the water-soluble organic solvent (e.g. an organic carboxylic acid), the adamantanol may be separated by cooling or concentrating a solution containing the mixture of the adamantanol and the group of adamantanepolyols in the mixed solvent to crystallize the adamantanol, or by adding water to a solution containing the mixture in the water-soluble organic solvent (or the mixed solvent), which may be heated if necessary, to crystallize the adamantanol.

The crystallized adamantanol can be recovered by a known separation process such as filtration or centrifugation. The thus recovered adamantanol can be purified to a further degree by recrystallization. After the recovery of the adamantanol, the group of adamantanepolyols, which is contained in the remaining mixture, can be recovered by a conventional process such as filtration, concentration, distillation, crystallization, extraction, recrystallization, column chromatography, and a combination of these.

In the case where the group of adamantanepolyols contain an adamantanediol, and an adamantanepolyol having at least three hydroxyl groups per molecule, these components can be separated by means of the above-mentioned separation Process A or B, directed to the separation of an adamantanediol and an adamantanepolyol. Consequently, the combination of Separation Processes C and A, or Separation Processes C and B, ensures the separation of an adamantanol, an adamantanediol, and an adamantanepolyol, from a mixture of these three components.

By way of illustration, each of an adamantanol, an adamantanediol, and an adamantanepolyol can be separated from the reaction mixture obtained in the above oxidation reaction using acetic acid or other water-soluble organic solvents as the reaction solvent. A process therefor is described hereinafter.

The process comprises concentrating the oxidation reaction mixture under atmospheric pressure or reduced pressure (e.g. about 20 to 45 Torr, preferably about 30 to 40 Torr, if the reaction solvent is acetic acid or the like) at a temperature (temperature of the reaction mixture) of about 40 to 60° C. (preferably about 45 to 55° C.), cooling the concentrate to a temperature of about 10 to 40° C. (e.g. room or ambient temperature), and adding water thereto for crystallization of the adamantanol. The concentration rate of the reaction mixture, which partly depends on the species of the reaction solvent, may be about 50 to 80% by weight. If the reaction solvent is acetic acid or the like, the rate is preferably about 60 to 65% by weight. The amount of water is about 200 to 500 parts by weight relative to 100 parts by weight of the concentrate. In this concentrate, the proportion of the water-soluble organic solvent relative to the water to be added is almost equivalent to the proportion of the water-soluble organic solvent relative to water in the preferable aqueous solvent as described above.

The thus crystallized adamantanol is filtered off and dried to give a crystal of adamantanol. This crystal can be further purified, for instance, by recrystallization with the use of a solvent such as hexane. In the recrystallization, the adamantanol should be dissolved in the solvent at a temperature of about 10 to 100° C., preferably about 15 to 60° C. Recrystallization at too high a dissolution temperature tends to result in an adamantanol with a lower purity.

After the filtration of the adamantanol, at least one organic solvent selected from esters or ketones and separable from water (e.g. ethyl acetate) is added to the filtrate for extraction. The amount of the organic solvent is about 50 to 1,000 parts by weight, preferably about 100 to 700 parts by weight, and more preferably about 200 to 500 parts by weight, relative to 100 parts by weight of the filtrate. Crystallisation of the adamantanediol occurs as a result of concentrating a separated organic layer, and, where necessary, adjusting the mixture composition or cooling the mixture. A highly purified adamantanediol is provided by washing or recrystallization of the crystallized adamantanediol with using a proper solvent [e.g. a mixed solvent of methanol and ethyl acetate (methanol/ethyl acetate=about 5/95 to 20/80, by weight)]. In the meantime, the adamantanepolyol is recovered by concentrating a water layer, and crystallizing the concentrate with a proper solvent or carrying out column chromatography.

[Separation of an Adamantanol and a Group of Adamantanepolyols by Crystallization (2) (Separation Process D)]

The adamantanol and the group of adamantanepolyols have different degrees of solubility also in organic solvents such as esters, ketones and cyclic ethers. Therefore, the adamantanol and the group of adamantanepolyols can be separated from each other, for instance, by concentrating or cooling a solution (heated, if necessary) containing a mixture of an adamantanol and a group of adamantanepolyols in at least one organic solvent selected from esters, ketones or cyclic ethers, thereby crystallizing the group of adamantanepolyol. This Separation Process D is applicable to the reaction mixture obtained by the above-mentioned oxidation reaction, or to the adamantanediol separated by Separation Process A and containing an adamantanol as an impurity.

As the esters, there may be mentioned aliphatic carboxylic acid esters (e.g. $C_{1-3}$ aliphatic carboxylic acid-$C_{1-4}$ alkyl esters such as methyl formate, ethyl formate, methyl acetate, ethyl acetate, isopropyl acetate, butyl acetate, and methyl propionate; $C_{1-3}$ aliphatic carboxylic acid-$C_{5-10}$ cycloalkyl esters such as cyclohexyl formate, cyclohexyl acetate, cyclooctyl acetate, and cyclopentyl propionate), aromatic carboxylic acid esters (e.g. $C_{7-8}$ aryl mono- or di-carboxylic acid-$C_{1-4}$ alkyl esters such as methyl benzoate, ethyl benzoate, and dimethyl phthalate), etc.

As the ketones, there may be exemplified, aliphatic ketones (e.g. $C_{1-4}$ alkyl-$C_{1-4}$ alkyl ketones such as acetone, methyl ethyl ketone, diethyl ketone, methyl isopropyl ketone, methyl isobutyl ketone, and diisopropyl ketone), alicyclic ketones (e.g. $C_{5-10}$ cycloalkanones such as cyclopentanone, cyclohexanone, methyl cyclohexanone, cycloheptanone, and cyclooctanone), etc. The cyclic ethers include tetrahydrofuran and dioxane, to name a few.

In the processes of the present invention, the organic solvents which have a solubility parameter δ of about 7.7 to 12.2 ($cal^{1/2}/cc^{1/2}$) may also be used as the crystallization solvent. The solubility parameter δ is preferably in the range of about 8.0 to 11.0 ($cal^{1/2}/cc^{1/2}$), and more preferably about 8.2 to 10.5 ($cal^{1/2}/cc^{1/2}$). As such organic solvents, there may be mentioned, for instance, not only the above-mentioned esters [e.g. methyl acetate (δ=9.6), ethyl acetate (δ=9.1), butyl acetate (δ=8.5)], the above-mentioned ketones [e.g. acetone (δ=10.0), methyl ethyl ketone (δ=9.3), diethyl ketone (δ=8.8), cyclohexanone (δ=9.7)], the above-mentioned cyclic ethers [e.g. dioxane (δ=9.9)]; but also alcohols [e.g. butanol (δ=11.4), cyclohexanol (δ=11.4), 2-ethylhexanol (δ=9.5)], nitriles [e.g. acetonitrile (δ=11.9), benzonitrile (δ=8.4)], aromatic hydrocarbons [e.g. benzene (δ=9.2), toluene (δ=8.9)], alicyclic hydrocarbons [e.g. cyclohexane (δ=8.2)], etc.

These organic solvents can be used alone or in combination of two or more species. As the crystallization solvent, the organic solvent only needs to comprise at least any of the above organic solvents, but, if necessary, the organic solvent may further comprise other kinds of solvents in addition to the above-mentioned ones (e.g. water-soluble solvents inclusive of acetic acid).

In this separation process, the temperature to dissolve the adamantanol and the group of adamantanepolyols in the organic solvent is the same as the one defined in Separation Process C.

The crystal of the group of adamantanepolyols can be recovered by a known separation process such as filtration or centrifugation. The group of adamantanepolyols thus recovered can be purified further by recrystallization. After the recovery of the group of adamantanepolyols, the adamantanol, which is contained in the remaining mixture, can be recovered by a conventional process such as filtration, concentration, distillation, crystallization, extraction, recrystallization, column chromatography, and a combination of these.

Incidentally, if the group of adamantanepolyols contains an adamantanediol, and an adamantanepolyol having at least three hydroxyl groups per molecule, they can be separated by means of Separation Process A or B, as in Separation Process C. Namely, the combination of Separation Processes D and A, or Separation Processes D and B, ensures the separation of an adamantanol, an adamantanediol, and an adamantanepolyol, from a mixture of these three components.

An adamantanemonool, an adamantanediol, and an adamantanepolyol are, as described above, useful as a raw material for highly functionalized materials (e.g. optical fibers, optical elements, optical lenses, holograms, optical discs, contact lenses and other optical materials, transparent resin coating compositions for organic glasses, electric conductive polymers, photosensitive materials, fluorescent materials). They are also useful as a raw material for introducing medicines which show high pharmacological activities or agricultural chemicals.

With the use of some specific solvents, the processes of the present invention ensure efficient separation of an adamantanemonool and a group of adamantanepolyols each having plural hydroxyl groups per molecule, or an adamantanediol and an adamantanepolyol having at least three hydroxyl groups per molecule from each other, by means of extraction, crystallization or the like. These processes can be conducted under mild or moderate conditions by a simple operation of extraction or separation (distribution).

Additionally, the process of the invention ensures efficient separation of an adamantanediol and an adamantanepolyol from the reaction mixture containing a group of adamantanepolyols obtained by oxidation with oxygen of a group of adamantanes in the presence of the imide compound.

The following examples are intended to describe the present invention in further detail and should by no means be interpreted as defining the scope of the invention.

EXAMPLES

Example 1

(Separation of an adamantanediol and an adamantanetriol)

In an oxygen atmosphere under 1 atm, a mixture of an adamantanol (3.045 g, 0.02 mole), N-hydroxyphthalimide (NHPI; 0.326 g, 0.002 mole), acetylacetonatocobalt(II) (0.030 g, 0.0001 mole), and acetic acid (32 ml) was stirred at 90° C. for 8 hours. Then, the acetic acid, the reaction solvent, was distilled off from the reaction mixture. The remaining mixture was washed using diisopropyl ether (200 ml) and filtered. To the resulting filtered cake, water (20 ml) and ethyl acetate (60 ml) were added. After the stirring of the mixture, the floating substances were filtered out. The filtrate was separated into a layer of water and a layer of ethyl acetate. The water layer was subjected to extraction for three times with the use of ethyl acetate (60 ml each). As a result, the combined ethyl acetate layer contained 1.661 g of an adamantanediol, while the water layer contained 0.055 g of an adamantanediol, and 0.573 g of an adamantanetriol.

Example 2

[Oxidation Reaction Step]

In a reactor equipped with a condenser, a sparger for air-supply, a thermometer, and stirring blades, acetic acid (15,000 g) was fed under a nitrogen atmosphere. With stirring, adamantane (1,200 g, 8.808 moles), NHPI (143.7 g, 0.8808 mole), and acetylacetonatovanadium(III) (3.068 g, 0.00881 mole) were further supplied in the reactor. The mixture was allowed to react at 85° C. for six hours under an air flow at 7 l/min. After the completion of the reaction, the reactor was purged with nitrogen, and cooled down to give a reaction mixture (16,200 g). A gas chromatographic analysis of the reaction mixture provided 40.1 g of the adamantane, 502.5 g of an adamantanol, 151.5 g of an adamantanone, 295.1 g of an adamantanediol, and 40.5 g of an adamantanetriol.

[Adamantanol Crystallizing Step]

The above reaction mixture was concentrated to 6,179 g under 40 Torr at a mixture temperature of 50° C. (concentration rate: 62%). The concentrate was cooled down to room temperature, added with water (18.5 kg) in the period of two hours, and then stirred at room temperature for two hours. The crystallized solid was filtered by suction and dried to give coarse crystals of the adamantanol. The coarse crystals, being analysed by gas chromatography, contained 35.2 g of the adamantane, 420.0 g of the adamantanol (recovery: 84%), 121.0 g of the adamantanone, and 18.7 g of the adamantanediol. The purity of the adamantanol was 67.0%. The filtrate (22.5 kg) contained 278.0 g of the adamantanediol (recovery: 94%), 30.2 g of the adamantanone, 80.5 g of the adamantanol, and 35.5 g of the adamantanetriol.

[Adamantanol Recrystallizing Step]

To the above-obtained coarse adamantanol crystals (236.8 g; adamantanol content 159.3 g), hexane (8 l) was added and the mixture was stirred at 60° C. for three hours. After the filtration of the undissolved substances, the filtrate was left overnight at room temperature. As a result, needle crystals of the adamantanol was obtained in 80.2 g (purity: 96.3%).

[Adamantanediol Extracting Step]

In an extraction column with a diameter of 80 mm and a length of 1,200 mm, the filtrate obtained in the adamantanol crystallizing step was supplied at a flow rate of 4 l/hr., together with ethyl acetate, as an extracting solvent, at a flow rate of 12 l/hr. Continuous extraction was thus carried out at room temperature (20° C). The extract was analysed by gas chromatography, and was proved to contain 255.8 g of the adamantanediol (recovery: 92%), 80.0 g of the adamantanol, and 29.8 g of the adamantanone.

[Adamantanediol Crystallizing Step]

The above-obtained extract (74,700 g) was concentrated to 1,550 g. To this concentrate, ethyl acetate (3.4 l) was added little by little at room temperature, and the mixture was stirred for 1.5 hours. Solid crystals were filtered by suction to give coarse crystals of the adamantanediol (264 g). Gas chromatography of the coarse crystals gave 228.3 g of the adamantanediol, and 16.7 g of the adamantanol. The purity of the adamantanediol was 88.3%.

[Adamantanediol Purifying Step]

A methanol (10% by weight)-ethyl acetate solution (680 ml) was added to the coarse adamantanediol crystals (264 g) at room temperature. The coarse crystals were washed after 1.5 hours of stirring. The crystals were sucked and filtered, and then dried to give white crystals of the adamantanediol (225 g, purity: 97.5%).

[Adamantanetriol Purifying Step]

The mixture remaining after the adamantanediol extracting step (15,300 g) was concentrated. Silica gel chromatography of the concentrate (extraction solvent: ethyl acetate-methanol) provided 29.8 g of the adamantanetriol.

Example 3

(Separation of an adamantanol and a group of adamantanepolyols)

A mixture of an adamantanol (50.0 g, 0.328 mole), NHPI (10.72 g, 0.0657 mole), acetylacetonatovanadium(III) (0.1144 g, 0.000328 mole), and acetic acid (300 ml) was stirred at 85° C. for eight hours, in an oxygen atmosphere under 1 atm. After the completion of the reaction, the reaction mixture was cooled and analysed by gas chromatography, which indicated that the mixture contained an unreacted adamantanol (4.0 g), an adamantanediol (29.2 g), and an adamantanetriol (16.5 g). To this reaction mixture which was concentrated to 90 g, ethyl acetate (1,500 ml) was added little by little at room temperature, and the mixture was stirred for one hour. The thus obtained crystals were filtered by suction, and dried to give crystals (27.5 g). A gas chromatographic analysis of the crystals showed that the crystals were composed of the adamantanediol (12.0 g) and the adamantanetriol (14.5 g).

Example 4

(Separation of an adamantanol and an adamantanediol)

An ethyl-acetate solution (10 kg) containing an adamantanediol (43.9 g), an adamantanol (16.7 g), an adamantanone (5.7 g) and acetic acid (800 g) was concentrated to 200 g. Ethyl acetate (600 ml) was added to the concentrate at 50° C. and stirred for one hour. After cooling the mixture, the crystallized solid was filtered by suction, and dried to give white crystals of the adamantanediol (37.9 g, purity: 96.3%).

What is claimed is:

1. A process for separating an adamantanemonool an adamantanediol, and adamantanepolyols having at least three hydroxyl groups per molecule, from a mixture of adamantanols each having at least one hydroxyl group per molecule, which process comprises the steps of:
   (ia) separating the adamantanemonool and a mixture of adamantanepolyols having a plurality of hydroxyl groups per molecule and containing the adamantanediol and the adamantanepolyols, from the mixture of adamantanols, by employing an aqueous solvent containing at least water, thereby exclusively crystallizing the adamantanemonool out of the aqueous solution containing the mixture of adamantanols, and
   (ii) separating the adamantanediol and the adamantanepolyols from a mixture remaining after the recovery of the adamantanemonool, by employing an aqueous solvent containing at least water, and at least one organic solvent selected from the group consisting of esters and ketones, thereby in a single step distributing the adamantanepolyols into an aqueous solvent layer and the adamantanediol into an organic solvent layer.

2. A process as claimed in claim 1, wherein said organic solvent is separable from the aqueous solvent.

3. A process as claimed in claim 1, wherein said organic solvent is at least one species selected from the group consisting of (1) aliphatic carboxylic acid esters, (2) aromatic carboxylic acid esters, (3) aliphatic ketones, and (4) alicyclic ketones.

4. A process as claimed in claim 1, wherein said aqueous solvent is water; and said organic solvent is at least one species selected from the group consisting of (1a) $C_{2-10}$ aliphatic carboxylic acid-$C_{1-10}$ alkyl esters, (1b) $C_{2-10}$ aliphatic carboxylic acid-aryl esters, (2) $C_{7-8}$ aryl mono- or di-carboxylic acid-$C_{1-6}$ alkyl esters, (3) $C_{1-4}$ alkyl-$C_{2-4}$ alkyl ketones, and (4) $C_{5-10}$ cycloalkanones.

5. A process as claimed in claim 1, wherein the proportion of the aqueous solvent relative to the organic solvent is such that the former/the latter (by weight) is 0.1/1 to 10/1.

6. A process as claimed in claim 1, wherein said process comprises the steps of allowing a reaction mixture obtained by an oxidaton reaction for producing the group of adamantanepolyols each having a plurality of hydroxyl groups per molecule to be subjected to washing or extraction with using at least one organic solvent selected from the group consisting of ethers and hydrocarbons, and distributing the resulting non-extracted components containing an adamantanediol and an adamantanepolyol.

7. A process as claimed in claim 1, wherein said process comprises the steps of allowing a reaction mixture obtained by oxidizing at least one substrate selected from the group consisting of adamantane and adamantanemonools to be subjected to washing or extraction with using at least one organic solvent selected from the group consisting of ethers and hydrocarbons, and extracting the resulting non-extracted components containing an adamantanediol and an adamantanepolyol with water and at least one organic solvent selected from the group consisting of esters and ketones and separable from said water, said oxidation reaction being conducted in the presence of an imide compound shown by the formula (1),

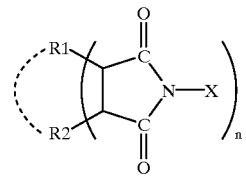

wherein $R^1$ and $R^2$ represent, same or different, a hydrogen atom, a halogen atom, an alkyl group, an aryl group, a cycloalkyl group, a hydroxyl group, an alkoxy group, a carboxyl group, an alkoxycarbonyl group or an acyl group; $R^1$ and $R^2$ may bond together to form a double bond or an aromatic or non-aromatic ring; X stands for an oxygen atom or a hydroxyl group; and n is an integer of 1 to 3.

8. A process as claimed in claim 1, wherein said aqueous solvent, which is employed in the step (ia), is water or a mixture of a water-soluble organic solvent and water, and wherein the proportion of the water-soluble organic solvent relative to the water is such that the former/the latter (by weight) is 0/100 to 50/50.

9. A process for separating an adamantanemonool, an adamantanediol, and adamantanepolyols having at least three hydroxyl groups per molecule, from a mixture of adamantanols each having at least one hydroxyl group per molecule, which process comprises the steps of:
   (1b) separating the adamantanemonool and a mixture of adamantanepolyols having a plurality of hydroxyl groups per molecule and containing the adamantanediol and the adamantanepolyols, from the mixture of adamantanols, by employing at least one organic solvent selected from the group consisting of esters, ketones and cyclic ethers, thereby exclusively crystallizing the mixture of adamantanepolyols out of a solution of said organic solvent containing the mixture of adamantanols,
   (ii) separating the adamantanediol and the adamantanepolyols from the mixture of adamantanepolyols, by employing an aqueous solvent containing at least water, and at least one organic solvent selected from the group consisting of esters and ketones, thereby in a single step distributing the adamantanepolyols into an aqueous solvent layer and the adamantanediol into an organic solvent layer.

10. A process as claimed in claim 9, wherein said organic solvent, which is employed in the step (ib) is an organic solvent having a solubility parameter δ of 7.7 to 12.2 $(cal^{1/2}/cc^{1/2})$.

11. A process as claimed in claim 1 or 9, wherein said process comprises allowing a reaction mixture obtained by an oxidation reaction for producing a group of adamantanols each having at least one hydroxyl group per molecule to be subjected to crystallization.

12. A process for separating an adamantanemonool, an adamantanediol, and an adamantanepolyol having at least three hydroxyl groups per molecule, from a mixture of adamantanols each having at least one hydroxyl group per molecule, wherein said process comprises the steps of subjecting a reaction mixture obtained by oxidizing at least one substrate selected from the group consisting of adamantane and adamantanemonools to crystallization using an aqueous solvent containing at least water of the adamantanemonool, and adding an organic solvent, selected from the group consisting of esters separable from water and ketones separable from water, to a mixture remaining after the recovery of the adamantanemonool, thereby in a single step distributing the adamantanediol into an organic solvent layer and the adamantanepolyol into an aqueous solvent layer, said oxidation reaction being conducted in the presence of an imide compound shown by the formula (1),

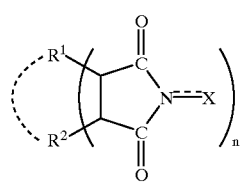

(1)

wherein $R^1$ and $R^2$ may be the same or different and represent a hydrogen atom, a halogen atom, an alkyl group, an aryl group, a cycloalkyl group, a hydroxyl group, an alkoxy group, a carboxyl group, an alkoxycarbonyl group or an acyl group; $R^1$ and $R^2$ may bond together to form a double bond or an aromatic or non-aromatic ring; X is an oxygen atom or a hydroxyl group; and n is an integer of 1 to 3.

13. A process as claimed in claim 1, wherein the proportion of the aqueous solvent relative to the organic solvent is 0.3/1 to 3/1.

* * * * *